United States Patent
Shingte et al.

(12)

(10) Patent No.: US 6,790,993 B1
(45) Date of Patent: Sep. 14, 2004

(54) 1,1-BIS(4-AMINOPHENYL)-3-ALKYLCYCLOHEXANES AND METHOD OF PREPARATION THEREOF

(75) Inventors: Rahul Diliprao Shingte, Maharashtra (IN); Prakash Purushottam Wadgaonkar, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/620,766

(22) Filed: Jul. 17, 2003

(51) Int. Cl.$^7$ ................. C07C 211/54; C07C 211/55
(52) U.S. Cl. ................................................ 564/322
(58) Field of Search ........................................ 564/322

(56) References Cited

U.S. PATENT DOCUMENTS 4,053,637 A * 10/1977 Carnmalm et al. ......... 514/650
4,103,030 A * 7/1978 Kojima et al. .............. 514/646
4,110,376 A * 8/1978 Kojima et al. .............. 564/322
4,141,993 A * 2/1979 Carnmalm et al. ......... 514/646
6,255,439 B1 * 7/2001 Avadhani et al. ........... 528/196

OTHER PUBLICATIONS

Database CAPLUS on STN, Acc. No. 1999:365724, Choi et al., JP 11152332 (Jun. 8, 1999) (abstract).*

* cited by examiner

Primary Examiner—Brian Davis
(74) Attorney, Agent, or Firm—Nixon & Vanderhye P.C.

(57) ABSTRACT

The present invention relates to new aromatic diamines. More particularly, the present invention relates to new aromatic diamines prepared from cashew nut shell liquid (CNSL), which is a renewable resource material. The present invention particularly relates to novel 1,1-bis(4-aminophenyl)-3-alkylcyclohexanes and to a method for their preparation.

26 Claims, No Drawings

1,1-BIS(4-AMINOPHENYL)-3-ALKYLCYCLOHEXANES AND METHOD OF PREPARATION THEREOF

FIELD OF THE INVENTION

The present invention relates to new aromatic diamines. More particularly, the present invention relates to new aromatic diamines prepared from cashew nut shell liquid (CNSL), which is a renewable resource material. The present invention particularly relates to novel 1,1-bis(4-aminophenyl)-3-alkylcyclohexanes and to a method for their preparation.

BACKGROUND OF THE INVENTION

Cashew nut shell liquid (CNSL) is known to contain compounds useful in several areas of chemical industry, such as plastics production. The level of interest in CNSL is evident by the fact that technical grade CNSL is a commercially available product. CNSL comprises a major proportion (typically about 80% by wt) of a material sold commercially under the trade name CARDANOL which comprises a mixture of 3-(pentadec-8-enyl)phenol, 3pentadec-8,11-dienyl)phenol and 3-(pentadec-8,11,14-trienyl)phenol. Minor constituents include about 18% by wt. of a material also sold separately under the trade name CARDOL, which is a mixture of the corresponding 5-substituted resorcinols, and about 2% by wt. of 2-methylcardol, which is a mixture of the corresponding 2-methyl-5-substituted resorcinols, and other materials.

The development of new aromatic diamines which are capable of providing polymers with high processability and are also useful in applications such as interlayer dielectrics, alignment liquid crystal films and light wave guide materials is an area of importance. It is known in the art that incorporating long alkyl chain in polyimide backbone provides materials with application in alignment liquid crystal films. It is therefore of great interest to synthesize new diamines with alkyl radical in their structure. It is also of importance and interest to develop aromatic diamines, which are easily and economically obtained from CNSL, since CNSL is readily available commercially and is also a renewable resource.

OBJECTS OF THE INVENTION

The main object of the invention is to provide new aromatic diamines from naturally occurring materials such as cashew out shell liquid.

It is another object of the invention to provide a class of novel 1,1-bis(4-aminophenyl)-3-alkylcyclohexanes, from naturally occurring materials such as cashew nut shell liquid.

It is another object of the invention to provide a process for the preparation of a class of novel 1,1-bis(4-aminophenyl)-3-alkylcyclohexanes, from naturally occurring materials such as cashew nut shell liquid.

It is another object of the invention to provide a simple process for synthesis of novel aromatic diamine starting from naturally occurring cashew nut shell liquid (CNSL) which is capable of providing processable polyimides, polyamides, polyazomethines and the like.

SUMMARY OF THE INVENTION

The present invention provides novel aromatic diamines synthesized from naturally occurring and renewable resources such as CNSL, which have application in manufacture of processable polymers polyimides, polyamides, polyazomethines and the like.

Accordingly, the present invention provides a 1,1-bis(4-aminophenyl)3-alkylcyclohexane of the formula I Formula I $$\left[ H_2N-\!\!\!\left\langle\bigcirc\right\rangle\!\!\!-\right]_2\!\!\!\left\langle\bigcirc\right\rangle\!\!\!-R$$

wherein R is an alkyl radical with at least 8 carbon atoms.

In one embodiment of the invention, R is pentadecyl.

The present invention also relates to a process for the preparation of 1,1-bis(4-aminophenyl)-3-alkylcyclohexane of the formula I.

Formula I $$\left[ H_2N-\!\!\!\left\langle\bigcirc\right\rangle\!\!\!-\right]_2\!\!\!\left\langle\bigcirc\right\rangle\!\!\!-R$$

wherein R is an alkyl radical with at least 8 carbon atoms, said process comprising:

(a) hydrogenating a composition comprising substituted phenols of the formula II Formula II $$HO-\!\!\!\left\langle\bigcirc\right\rangle\!\!\!-R'$$

wherein R' is an alkyl or alkenyl radical containing at least 8 carbon atoms, to the corresponding substituted cyclohexanols;

(b) oxidizing the substituted cyclohexanols to corresponding cyclohexanones; and (c) reacting the cyclohexanones obtained in step (b) with aniline in the presence of an acidic catalyst to obtain the compound of formula I.

In one embodiment of the invention, R' is selected from the group consisting of pentadecyl, $C_{15}$ mono-olefinic radical, $C_{15}$ di-olefinic radical, $C_{15}$ tri-olefinic radical and any mixture thereof.

In another embodiment of the invention, the composition of step (a) is cashew nut shell liquid.

In another embodiment of the invention, step (A) is carried out at a temperature in the range of 120–150° C. and a pressure in the range of 500–700 psi, in the presence of a Group VIII metal catalyst.

In yet another embodiment of the invention, the Group VIII metal is ruthenium.

In yet another embodiment of the invention, the oxidation of step (b) is carried out using an oxidizing agent selected from the group consisting of hexavalent chromium compound, a peroxide and molecular oxygen.

In another embodiment of the invention, the oxidising agent is pyridinium chlorochromate.

In still another embodiment of the invention, step (b) is carried out at room temperature.

In another embodiment of the invention, the acidic catalyst used in step (c) is selected from acidic clay and hydrogen chloride.

In still another embodiment of the invention, step (c) is carried out at a temperature in the range of 140–160° C.

The present invention also relates to a process for the preparation of 1,1-bis(4-aminophenyl)-3-pentedecylcyclohexane, comprising:

(a) hydrogenating a composition comprising 3-pentadecylphenol obtained from cashew nut shell liquid to 3-pentadecylcyclohexanol, in the presence of a ruthenium catalyst, (b) oxidizing 3-pentatecylcyclohexanol to 3-pentdecylcyclohexanone with an oxidizing agent;

(c) reacting 3pentdecylcyclohexanone with aniline in the presence of an acidic catalyst to obtain 1,1-bis(4-aminophenyl)3-pentedecylcyclohexane.

In another embodiment of the invention, step (a) is carried out at a temperature in the range of 120–150° C. and a pressure in the range of 500–700 psi.

In yet another embodiment of the invention, the oxidizing agent is selected from the group consisting of hexavalent chromium compound, a peroxide and molecular oxygen.

In another embodiment of the invention, the oxidising agent is pyridinium chlorochromate.

In still another embodiment of the invention, step (b) is carried out at room temperature.

In another embodiment of the invention, the acidic catalyst used in step (c) is selected to from acidic clay and hydrogen chloride.

In still another embodiment of the invention, step (c) is carried out at a temperature in the range of140–160° C.

DETAILED DESCRIPTION OF THE INVENTION

The present invention relates to novel class of compounds 1,1-bis(4-aminophenyl)3-alkylcyclohexanes which have potential application in manufacture of processible polymers required in for example, alignment liquid crystal films. The compounds of the invention are of formula I

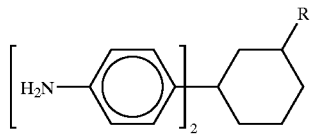

Formula I where R is an alkyl radical containing at least 8, and preferably to 8 to 18 carbon atoms Normal alkyl radicals are preferred. For example, the most preferred due to its availability in CNSL is the n-pentadecyl ($C_{15}H_{31}$) radical.

The compounds of formula I, viz. 1,1-bis(4-aminophenyl)-3-alkylcyclohexanes are prepared by first hydrogenating a composition comprising substituted phenols of formula II

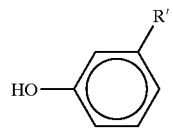

Formula II

The R' radical is an alkyl or alkenyl radical, the latter being converted by hydrogenation to the corresponding alkyl radical concurrently with the hydrogenation of the aromatic ring. In a preferred embodiment, the composition being hydrogenated contains at least one component of CNSL, particularly one or more of components of CARDANOL or hydrogenation products thereof and especially 3-pentadecylphenol. Thus R' is preferably pentadecyl, or a C15 mono-, di-, or triolefinic radical, or a mixture of any of the above.

The latter can be prepared by hydrogenation of the CARDANOL composition of constituents thereof and is also available commercially as so prepared from Cardolite Corp. Typically, hydrogenation conditions include temperatures in the range of 140–160° C., pressures in the range of 500–1000 psi, and use of a catalyst, typically a Group VIII metal catalyst such as Raney nickel. Suitable conditions are disclosed for example in Indian Patent 178216 Madhusudan et al., *Ind. J. Tech.*, 1973, 347–350, the disclosures of which are incorporated herein by reference.

Any hydrogenation conditions effective to saturate an aromatic radical can be employed in the step of hydrogenation. Typical conditions include the presence of catalysts, especially Group VIII metal catalysts such as supported ruthenium or nickel. Suitable supports include carbon, silica, alumina, silica-alumina, aluminum phosphate, calcium phosphate, zinc aluminate and zinc titanate. Other conditions such as temperature and pressure can vary depending on the catalyst used. For example, in the case of Raney nickel or ruthenium on carbon, pressures in the range of about 500–1000 psi, preferably 500–700 psi and temperatures in the range of 120–150° C. are typical. As noted herein above, some of the same catalysts can be used to reduce the CARDANOL constituents to pentadecylphenol under milder conditions. Illustrative of conditions for the hydrogenation of the first step of the process of the invention are U.S. Pat. No. 4,503,273 and Sethi et al., *Ind. J. Chem.*, 1964, 178–181, which are also incorporated herein by reference.

The second step of the process of the invention comprises oxidizing the cyclohexanol obtained after hydrogenation, to the corresponding cyclohexanone. The oxidizing agent employed can be any oxidizing agent capable of oxidizing the hydroxy radical to a ketone group. Illustrative oxidizing agents include hexavalent chromium compounds such as sodium dichromate and pyridinium chlorochromate, hypochlorites such as calcium hypochlorite, peroxides such as hydrogen peroxide and t-butyl hydroperoxide and molecular oxygen, optionally activated by microwave radiation or the like. Pyridinium chlorochromate adsorbed on silica gel is particularly useful. The reaction temperatures for the oxidation step depend on the oxidizing agent employed. For hexavalent chromium compounds, the temperatures are typically in the range of 35–80° C. The amount of oxidizing agent is most often a slight excess over the stoichiometric amount, typically about a 10–25% excess.

The final step comprises of contacting the cyclohexanone obtained after oxidation with aniline under reaction producing conditions. Such conditions include the presence of an acidic catalyst, for example aqueous hydrogen chloride, acidic clays, or hydrochloric acid in the form of aniline hydrochloride. Temperatures in the rate of 140–160° C. are typical. The intermediates and product in each step of the reaction can be worked up and isolated by any conventional means, such as solvent removal when a solvent is employed, washing, drying and recrystallization.

The invention will now be described by the following examples which are illustrative and should not be construed as limiting the scope of the invention in any manner.

EXAMPLE 1

A solution of 30.8 g (100 mmol) of 3-pentadecylphenol prepared from CNSL in 140 ml of isopropanol was taken in a 300 ml Parr reactor and 1.0 g of ruthenium on carbon was added. The reactor was pressurized with hydrogen at 600 psi and heated at 140° C. until absorption of hydrogen ceased (about 25 hours). The catalyst was removed by filtration, solvent distilled off, and product was dried at vacuum. The compound obtained was 3-pentadecylcyclohexanol in a yield of 31.0 g (99% of theoretical).

EXAMPLE 2

Pyridinium chlorochromate 21.0 g (96 mmol) was fined ground with 21.0 g of silica gel, 100–200 mesh and was suspended in 400 mL of dichloromethane with stirring and a solution of 20.0 g (64 mmol) of 3-pentadecylcyclohexanol in 100 mL of dichloromethane was added at room temperature. The reaction was allowed to continue for two hours. The reaction mixture was filtered and solution was passed through a column of celite and silica gel to give colorless filtrate. The solvent was distilled off to go desired 3-pentadecylcyclohexanone as a waxy solid. Yield was 19.12 g (96% of theoretical).

EXAMPLE 3

A 100 mL single necked flask fitted with a magnetic stirrer and a reflux condenser was charged with a 10.0 g (32 mmol) of 3-pentadecylcyclohexanone, 8.4 g (65 mmol) aniline hydrochloride and 12.05 g (130 mmol) of aniline. The resulting mixture was refluxed at 140° C. for 10 hours under positive pressure of nitrogen. The reaction mixture was cooled to room temperature, diluted with dichloromethane, and washed with aqueous sodium hydroxide solution and water and dried over sodium sulfate. Solvent was distilled off and excess aniline removed under vacuum. The desired 1,1-bis(4-aminophenyl)-3-pentadecylcyclohexan was obtained in a yield of 5.4 g (35% of theoretical). M.p. 107° C.

ADVANTAGES OF THE INVENTION

The present invention provides a simple procedure for the synthesis of a novel aromatic diamine starting from naturally occurring compound CNSL, which has the potential to provide processible polyimide polyamides, polyazomethines, etc.

The process of the invention is simple and easy to work up.

The process of the invention is economical, since it uses a naturally occurring and renewable resourse CNSL.

We claim:

1. 1,1-bis(4-aminophenyl)-3-alkylcyclohexane of the formula I

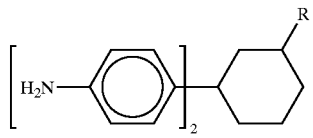

Formula I wherein R is an alkyl radical with at least 8 carbon atoms.

2. 1,1-bis(4-aminophenyl)-3-alkylcyclohexane as claimed in claim 1 wherein R is an alkyl radical with 8 to 18 carbon atoms.

3. A 1,1-bis(4-aminophenyl)3-alkylcyclohexane as claimed in claim 1 wherein R is pentadecyl.

4. A process for preparing 1,1-bis(4-aminophenyl)3-alkylcyclohexane of the formula I

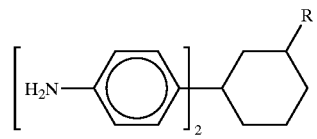

Formula I wherein R is an alkyl radical with at least 8 carbon atoms, said process comprising:
(a) hydrogenating a composition comprising substituted phenols of the formula II

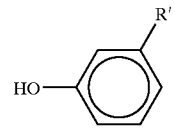

Formula II wherein R' is an alkyl or alkenyl radical containing at least 8 carbon atoms, to the corresponding substituted cyclohexanols;
(b) oxidizing the substituted cyclohexanols to corresponding cyclohexanones; and
(c) reacting the cyclohexanone obtained in step (b) with aniline in the presence of an acidic catalyst to obtain the compound of formula I.

5. A process as claimed in claim 4 wherein R' is selected from the group consisting of pentadecyl, $C_{15}$ mono-olefinic radical, $C_{15}$ di-olefinic radical, $C_{15}$ tri-olefinic radical and any mixture thereof.

6. A process as claimed in claim 4 wherein the composition of step (a) is cashew nut shell liquid.

7. A process as claimed in claim 4 wherein step (a) is carried out at a temperature in the range of 120–160° C. and a pressure in the range of 500–1000 psi and in the presence of a Group VIII metal catalyst.

8. A process as claimed in claim 7 wherein the Group VIII metal is selected from ruthenium and nickel.

9. A process as claimed in claim 7 wherein the Group VIII metal catalyst is provided on a support.

10. A process as claimed in claim 9 wherein the support is selected from the group consisting of carbon, silica, alumina, silica-alumina, aluminum phosphate, calcium phosphate, zinc aluminate and zinc titanate.

11. A process as claimed in claim 4 wherein the oxidation of step (b) is carried out using an oxidizing agent selected from the group consisting of hexavalent chromium compound, a hypochlorite, a peroxide and molecular oxygen.

12. A process as claimed in claim 11 wherein the hexavalent chromium compound is selected from sodium dichromate and pyridinium chlorochromate.

13. A process an claimed in claim 11 wherein the hypochlorite comprises calcium hypochlorite.

14. A process as claimed in claim 11 wherein the peroxide is selected from hydrogen peroxide and t-butyl peroxide.

15. A process as claimed in claim 4 wherein step (b) is carried out at room temperature.

16. A process as claimed in claim 4 wherein the acidic catalyst used in step (c) is selected from acidic clay, aqueous hydrogen chloride and aniline hydrochloride.

17. A process as claimed in claim 4 wherein step (c) is carried out at a temperature in the range of 140–160° C.

18. A process for the preparation of 1,1-bis(4-aminophenyl)-3-pentedecylcyclohexane, comprising:

(a) hydrogenating a composition comprising 3-pentadecylphenol obtained from cashew nut shell liquid to 3-pentadecylcyclohexanol, in the presence of a ruthenium catalyst;

(b) oxidizing 3-pentadecylcyclohexanol to 3-pentdecylcyclohexanone with an oxidizing agent;

(c) reacting 3-pentdecylcyclohexanone with aniline in the presence of an acidic catalyst to obtain 1,1-bis(4-aminophenyl)3-pentedecylcyclohexane.

19. A process as claimed in claim 18 wherein step (a) is carried out at a temperature in the range of 120–160° C. and a pressure in the range of 500–1000 psi.

20. A process as claimed in claim 18 wherein the oxidation of step (b) is carried out using an oxidizing agent selected from the group consisting of hexavalent chromium compound, a hypochlorite, a peroxide and molecular oxygen.

21. A process as claimed in claim 20 wherein the hexavalent chromium compound is selected from sodium dichromate and pyridinium chlorochromate.

22. A process as claimed in claim 20 wherein the hypochlorite comprises calcium hypochlorite.

23. A process as claimed in claim 20 wherein the peroxide is selected from hydrogen peroxide and t-butyl peroxide.

24. A process as claimed in claim 18 wherein step (b) is carried out at room temperature.

25. A process as claimed in claim 18 wherein the acidic catalyst used in step (c) is selected from acidic clay, aqueous hydrogen chloride and aniline hydrochloride.

26. A process as claimed in claim 18 wherein step (c) is carried out at a temperature in the range of 140–160° C.

* * * * *